(12) United States Patent
Boisart

(10) Patent No.: US 9,476,073 B2
(45) Date of Patent: Oct. 25, 2016

(54) RECOMBINANT MICROORGANISM

(71) Applicant: CARBIOS, Saint-Beauzire (FR)

(72) Inventor: Cédric Boisart, Fontaine-Mâcon (FR)

(73) Assignee: CARBIOS, Saint-Beauzire (FR)

( * ) Notice: Subject to any disclaimer, the term of this patent is extended or adjusted under 35 U.S.C. 154(b) by 0 days.

(21) Appl. No.: 14/387,285

(22) PCT Filed: Mar. 27, 2013

(86) PCT No.: PCT/EP2013/056583
§ 371 (c)(1),
(2) Date: Sep. 23, 2014

(87) PCT Pub. No.: WO2013/144239
PCT Pub. Date: Oct. 3, 2013

(65) Prior Publication Data
US 2015/0056673 A1 Feb. 26, 2015

(30) Foreign Application Priority Data
Mar. 27, 2012 (FR) ...................... 12 52733

(51) Int. Cl.
*C12P 7/62* (2006.01)
*C12N 9/54* (2006.01)
*C12P 7/56* (2006.01)
*C12P 39/00* (2006.01)

(52) U.S. Cl.
CPC ............. *C12P 7/625* (2013.01); *C12N 9/54* (2013.01); *C12P 7/56* (2013.01); *C12P 39/00* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 5,426,047 A * | 6/1995 | Ito | ........................ | C12N 15/746 435/252.3 |
| 6,429,006 B1 * | 8/2002 | Porro | ................... | C07K 14/395 435/254.2 |
| 7,465,575 B2 * | 12/2008 | Nilsson | .............. | A23C 19/0323 424/93.45 |
| 7,534,597 B2 * | 5/2009 | Hause | ..................... | C12N 1/16 435/134 |
| 7,960,154 B1 * | 6/2011 | Nakajima | .............. | C08J 11/105 435/183 |
| 8,137,953 B2 * | 3/2012 | Miller | .................. | C12N 9/0006 435/254.2 |
| 8,614,076 B2 * | 12/2013 | Wada | .................... | C12N 9/0006 435/139 |
| 8,859,260 B2 * | 10/2014 | Sawai | .................. | C12N 9/0006 435/254.2 |
| 2011/0008855 A1 * | 1/2011 | Park | ..................... | C12N 9/1025 435/135 |
| 2015/0290840 A1 | 10/2015 | Boisart et al. | | |

FOREIGN PATENT DOCUMENTS

| | | |
|---|---|---|
| CN | 101 457 218 | 6/2009 |
| JP | 2007 319092 | 12/2007 |
| WO | WO 2014/079844 | 5/2014 |

OTHER PUBLICATIONS

Bernard et al. FEBS lett. (1991) 290 (1-2), pp. 61-64.*
Matsuda, E. et al. "Gene Cloning and Molecular Characterization of an Extracellular Poly($_L$-Lactic Acid) Depolymerase from *Amycolatopsis* sp. Strain K104-1" *Journal of Bacteriology*, Nov. 2005, pp. 7333-7340, vol. 187, No. 21.
Database WPI, Accession No. 2009-K99963, Jun. 17, 2009, pp. 1-2, XP-002690934.
Database WPI, Accession No. 2008-F66138, Dec. 13, 2007, pp. 1-2, XP-002690935.
Wang, Z.-Y. et al. "Gene Cloning and Characterization of a Poly($_L$-Lactic Acid) Depolymerase from *Pseudomonas* sp. Strain DS04-T" *J Polym Environ*, Aug. 28, 2011, pp. 827-833, vol. 19, No. 4.
Akutsu-Shigeno, Y. et al. "Cloning and Sequencing of a Poly($_{DL}$-Lactic Acid) Depolymerase Gene from *Paenibacillus amylolyticus* Strain TB-13 and Its Functional Expression in *Escherichia coli*" *Applied and Environmental Microbiology*, May 2003, pp. 2498-2504, vol. 69, No. 5.
Petrov, K. et al. "$_L$(+)-Lactic acid production from starch by a novel amylolytic *Lactococcus lactis* subsp. *lactis* 884" *Food Microbiology*, Jun. 2008, pp. 550-557, vol. 25.
Currently pending claims of U.S. Appl. No. 14/443,524, 2016, pp. 1-4.

* cited by examiner

*Primary Examiner* — Nashaat Nashed
(74) *Attorney, Agent, or Firm* — Saliwanchik, Lloyd & Eisenschenk

(57) ABSTRACT

The invention concerns a microorganism which is genetically modified so as to i) synthesize an organic monomer by fermentation of a carbon source, and ii) depolymerize a polymer constituted at least by an organic monomer which it is capable of synthesizing. The invention also concerns a method for producing an organic monomer using a genetically modified microorganism of this type, as well as the coculture of this microorganism with another microorganism which is capable of synthesizing a polymer of interest.

11 Claims, 5 Drawing Sheets

RECOMBINANT MICROORGANISM

CROSS-REFERENCE TO RELATED APPLICATION

This application is the U.S. national stage application of International Patent Application No. PCT/EP2013/056583, filed Mar. 27, 2013.

The Sequence Listing for this application is labeled "Seq-List.txt" which was created on Sep. 13, 2014 and is 18 KB. The entire content of the sequence listing is incorporated herein by reference in its entirety.

FIELD OF THE INVENTION

The invention relates to a recombinant microorganism for the production of organic monomers for use in the synthesis of polymers. More precisely, the invention relates to a microorganism which has been genetically modified so as to produce monomers of this type from a carbon source, but also through depolymerization of polymers present in the culture medium. The invention also relates to a method for producing monomers using recombinant microorganisms of this type, as well as to a method for synthesizing polymers from the monomers produced.

PRIOR ART

Polymers are used in a large number of technical fields, in particular in the form of plastic material, including food packaging, the medical field, clothing, the automobile industry, etc. As an example, polyamides, and more particularly nylons, are used both for the manufacture of soles for shoes and in the form of microfilaments for surgical sutures. Similarly, certain polyesters (for example polyethylene terephthalate (PET), polylactic acid (PLA), etc.) are used in the manufacture of clothes and packaging, but also in the form of a thermoset resin for the manufacture of automobile or other parts.

Until recently, the polymers used in the majority of industries were obtained from non-renewable fossil energy sources such as oil. However, the difficulties associated with recycling such polymeric materials and the ever-increasing dearth of non-renewable fossil energy renders using them ever more questionable.

Thence, for a number of years, the manufacture of polymers from renewable raw materials or from biomass has been under development. Polylactic acid (PLA), for example, is a biodegradable polymer produced from lactic acid which has mechanical properties which are comparable to those of polymers obtained from the petrochemical industry. Microorganisms have been isolated and/or developed for their capacity to produce organic monomers and/or polymers from a suitable renewable carbon source.

As an example, various microorganisms have been developed to produce lactic acid from carbon sources such as starch, pentoses, etc. In particular, recombinant yeasts expressing a lactate dehydrogenase have been produced in order to synthesize lactic acid in an appropriate culture medium (WO 03/102152).

Similarly, yeasts have been genetically modified in order to express a fumarate reductase and to produce succinic acid from fumaric acid (WO 2009/065778).

Usually, such microorganisms, recombinant or otherwise, have to be cultured in a suitable culture medium comprising expensive substrates (glucose, saccharose, etc.). In order to improve the production performance of such microorganisms, it is also necessary to optimize the culture conditions (temperature, stirring, nature of the carbon source, etc.), which tends to further increase the production costs.

In order to reduce the production costs, attempts have been made to produce these metabolites directly from biomass which cannot be upgraded directly, such as sugar beet juice (WO 2008/000699), date juice (Boudjelal et al., Rev. Energ. Ren., Production et Valorisation-Biomasse [Biomass—Production and Upgrading], 2001, 41-46), etc. However, the pre-treatment of biomass to promote the growth of microorganisms therein is complicated and lengthy, which means that the production costs cannot be brought down in a satisfactory manner.

Further, the quantity of organic monomers produced by the microorganisms only exceeds 30 g/liter with difficulty, even under optimal culture conditions.

In addition, the quantity of organic monomers and/or associated polymers produced by the microorganisms is still relatively low and the associated costs are too high for it to be a real alternative to polyethylene (PE) and other petrochemical polymers. Although the idea of producing polymers from renewable sources is seductive, there is currently no system for production by fermentation which overcomes the problems of cost and/or yield and which can satisfactorily respond to demand.

SUMMARY OF THE INVENTION

The aim of the invention is to at least partially overcome at least one of the problems discussed above by proposing a recombinant microorganism which is capable of producing large quantities of organic monomers for use in the synthesis of polymers.

To this end, the invention proposes a microorganism, in particular a bacterium, a yeast or a fungus, which is genetically modified so as to be capable of synthesizing one or more monomer(s) by fermentation of a carbon source and depolymerizing, simultaneously or otherwise, a polymer present in the culture medium so as to liberate the monomers of which it is composed therefrom. The monomers produced thereby by that same microorganism derive from two different and independent sources. Furthermore, the use of a microorganism of this type means that the polymers can be recycled, and thus problems with the accumulation of plastic waste can be overcome. Indeed, the polymers which are capable of being depolymerized by the microorganism of the invention can both be integrated into a product manufactured from plastic material and also be directly available in the culture medium, in solution or otherwise.

Advantageously, the microorganism of the invention is capable of depolymerizing high-molecular-weight polymers, not only into oligomers with a lower molecular weight, but right down to the building block or monomer.

Thus, the invention concerns a microorganism which is genetically modified so as to:
  i) synthesize an organic monomer by fermentation of a carbon source, and
  ii) depolymerize a polymer constituted at least by organic monomers which it is capable of synthesizing.

The invention also concerns a method for producing an organic monomer, comprising the steps of:
  contacting a microorganism according to the invention with a carbon source and with a polymer which is capable of being depolymerized by said microorganism, and optionally
  recovering the organic monomer produced.

The invention also envisages a coculture of microorganisms comprising at least a first microorganism in accordance with the invention and at least a second microorganism, optionally genetically modified, which is capable of synthesizing a polymer constituted at least by monomers produced by the first microorganism.

The invention also concerns a method for synthesizing polymers using a coculture of microorganisms in accordance with the invention, comprising the steps of:
  contacting the coculture of microorganisms with a carbon source and with a polymer which is capable of being degraded by the first microorganism, and optionally recovering the polymer produced by the second microorganism.

DETAILED DESCRIPTION

Figure 1:
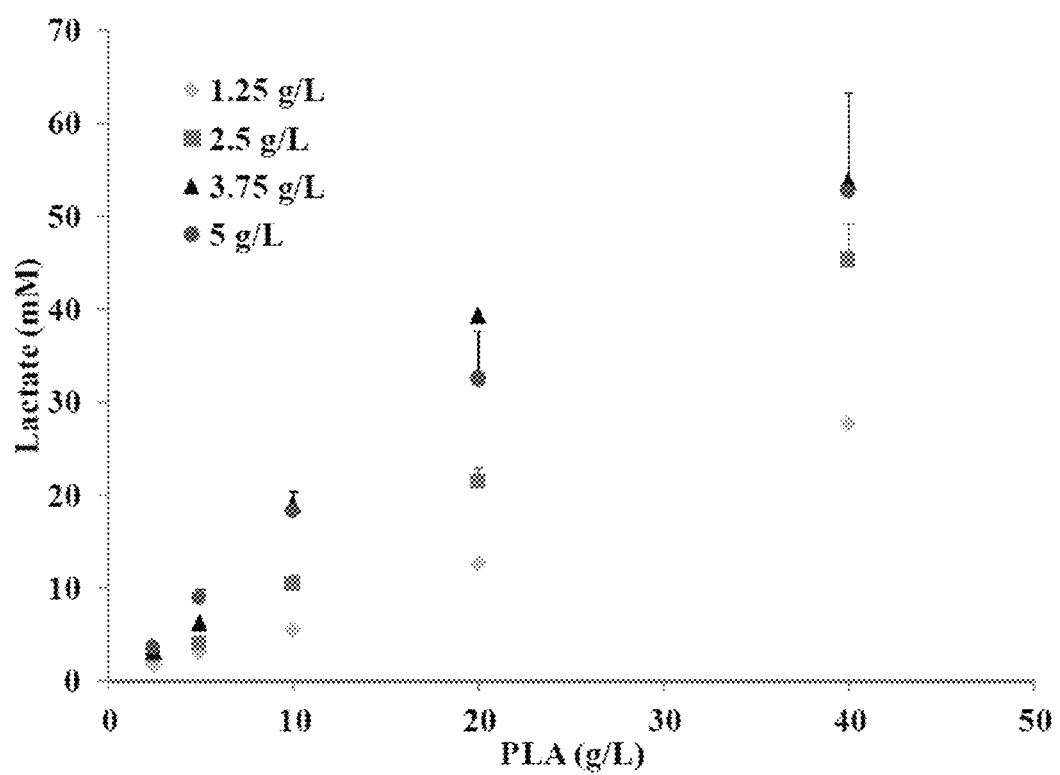
FIG. 1: degradation of PLA to lactic acid in the presence of four levels of concentration of proteinase K (✦ 1.25 g/L, ✱ 2.5 g/L, ▲ 3.75 g/L, ✸ 5 g/L).

In the context of the invention, the term "microorganism" means any unicellular eukaryotic organism such as yeasts, microalgae and fungi, or prokaryotic organism such as bacteria.

Preferably, the microorganism is a microorganism from a genus selected from *Aspergillus, Cupriavidus, Clostridium, Corynebacterium, Escherichia, Pseudomonas, Yarrowia, Aeromonas, Candida, Burkholderia, Thermobifida, Fusarium, Pichia, Saccharomyces* and *Bacillus*. Preferably, the microorganism is selected from *Aspergillus Niger, Cupriavidus necator, Clostridium acetobutylicum, Corynebacterium glutamicum, Escherichia coli, Pseudomonas aeruginosa, Pseudomonas putida, Pseudomonas entomophila, Pseudomonas oleovorans, Yarrowia lipolytica, Aeromonas hydrophila, Candida tropicalis, Candida antartica, Burkholderia xenovorans, Burkholderia mallei, Burkholderia pseudomallei, Thermobifida fusca, Fusarium solani, Pichia pastoris, Saccharomyces cerevisiae, Bacillus subtilis* and *Bacillus megaterium*.

The term "genetically modified" microorganism means that the genome of the microorganism has been modified in a manner such that said microorganism exhibits two pathways, of synthesis and of depolymerization. As an example, the microorganism may be a microorganism which is naturally capable of synthesizing a monomer of interest from a carbon source and which is genetically modified to express the enzyme or enzymes necessary for the desired depolymerization, or vice versa. The microorganism may also not naturally exhibit any of the desired synthesis and depolymerization pathways, and be genetically modified for these two pathways. The microorganism may also naturally have one and/or the other of these pathways and be genetically modified to promote and/or enhance the expression of the genes involved. In accordance with the invention, the genome of the microorganism is modified so as to integrate at least one nucleic sequence coding for at least one enzyme involved in the pathway for biosynthesis of an organic monomer and/or in the depolymerization of a polymer, or coding for a biologically active fragment thereof. Said nucleic sequence may have been introduced into the genome of said microorganism or one of its ancestors using any suitable molecular cloning method. In the context of the invention, the "genome of a microorganism" means all of the genetic material contained in said microorganism, including the extrachromosomal genetic material contained, for example, in the plasmids, episomes, synthetic chromosomes, etc. The nucleic sequence introduced may be a heterologous sequence, i.e., it does not exist in the natural state in said microorganism, or a homologous sequence. Advantageously, a transcriptional unit is introduced into the genome of the microorganism which comprises the nucleic sequence of interest, placed under the control of one or more promoter(s).

The carbon source used by the microorganism of the invention preferably comprises refined sugars such as glucose, galactose, xylose, saccharose, etc., but also any organic material of vegetable or animal origin, or biomass, which is capable of being degraded by the microorganism to produce fermentable sugars. Thus, the carbon source may comprise hemicellulosic, cellulosic, lignocellulosic, etc. biomass, for example molasses and/or sugar cane bagasse, sugar refinery waste water or spent liquor, sugar crystallization mother liquors, etc. The carbon source may also comprise glycerol or oils (triglycerides). In all cases, the carbon source does not include the monomer produced by depolymerization of the polymer of the invention.

The simultaneous fermentation and depolymerization characteristic of the present invention is defined by the fact that the microorganism is brought into contact with the carbon source and the polymer at the same time (or within a very short time period, for example on the order of 15 minutes maximum), under the same physico-chemical conditions (for example temperature, pH and/or culture medium). Thus, the organic monomer produced by the two pathways (fermentation and depolymerization) may be recovered simultaneously in the culture medium.

The term "organic monomer" means an aliphatic or aromatic monomer essentially composed of carbon atoms and hydrogen. It generally comprises 1 to 8 carbon atoms, preferably 2 to 6 carbon atoms. The organic monomer may also comprise at least one heteroatom such as nitrogen or oxygen, generally in the form of an acid, alcohol, amine function, etc.

An organic monomer of the invention may in particular be a dicarboxylic acid or one of its derivatives such as an acid dianhydride, a diol, a hydroxylated acid such as α-hydroxylated acids, a diester, a lactone, a cyclic diester (glycolide, lactide, etc.), a diamine or a hydroxylamine.

A non-limiting list of these monomers is constituted by lactic acid, glycolic acid, 3-hydroxybutyric acid, 4-hydroxyvaleric acid, butanediol, propanediol, ethylene glycol, succinic acid, glutaric acid, adipic acid, terephthalic acid, furandicarboxylic acid, caprolactone, caprolactam, putrescine, cadaverine, hexamethylene diamine, esters, esteramides, etc.

The term "oligomer" means a succession of monomers in accordance with the invention comprising more than one monomer, and fewer monomers than the polymer supplied to the microorganism.

Polymers which are capable of being depolymerized by the microorganism of the invention are polymers the principal chain of which is essentially constituted by carbon atoms, and in particular polyesters and/or polyamides. The polymers of the invention may be homopolymers or copolymers, which may be branched. The polyesters may be aliphatic and/or aromatic. Examples of aliphatic polyesters which may be cited are polylactic acid (PLA), polyhydroxyalkanoates (PHAs), poly(butylene succinate) (PBS), poly(butylene succinate-co-adipate) (PB SA) or poly-β-caprolactone (pCAPA). Aliphatic polyesters which may in particular be cited are poly(ethylene terephthalate) (PET), poly(trimethylene terephthalate) (PTT), poly(butylene terephthalate) (PBT) or poly(butylene-adipate-terephthalate) (PBAT). Polyamides which may in particular be cited include poly(caprolactam) or nylon-6; poly(undecanamide) or nylon-11; or poly(hexamethylenediamine-adipate) or nylon-6,6.

The invention in particular envisages the depolymerization of aliphatic polyesters and the synthesis of all or a part of the esterification intermediates, acid and/or alcohol of said polyester, such as the depolymerization of polylactic acid (PLA) and the synthesis of lactic acid; the depolymerization of poly(3-hydroxybutyrate) (PHB) and the synthesis of 3-hydroxybutyric acid; the depolymerization of poly(3-hydroxybutyrate-co-4-hydroxyvalerate) (PHBV) and the synthesis of 3-hydroxybutyric acid and/or 4-hydroxyvaleric acid; the depolymerization of poly(butylene succinate) (PBS) and the synthesis of 1,4-butanediol and/or succinic acid; and the depolymerization of poly(butylene succinate-co-adipate) (PBSA) and the synthesis of 1,4-butanediol and/or succinic acid and/or adipic acid.

The invention also envisages the depolymerization of aromatic polyesters and the synthesis of all or part of the associated monomers, such as the depolymerization of poly(ethylene terephthalate) (PET) and the synthesis of ethylene glycol and/or terephthalic acid; the depolymerization of poly(trimethylene terephthalate) (PTT) and the synthesis of 1,3-propanediol and/or terephthalic acid; the depolymerization of poly(butylene terephthalate) (PBT) and the synthesis of 1,4-butanediol and/or terephthalic acid; and the depolymerization of poly(butylene adipate terephthalate) (PBAT) and the synthesis of 1,4-butanediol and/or adipic acid and/or terephthalic acid.

The invention also envisages the depolymerization of polyamides and the synthesis of all or a part of the associated monomers, such as the depolymerization of poly(caprolactam) or nylon-6 and the synthesis of caprolactam or 6-amino-hexanoic acid; the depolymerization of poly(undecanamide) or nylon-11 and the synthesis of undecanamide; and the depolymerization of poly(hexamethylenediamine-adipate) or nylon-6,6 and the synthesis of hexamethylenediamine and/or adipic acid.

In accordance with the invention, the same microorganism is capable of synthesizing at least one organic monomer and depolymerizing a polymer constituted at least by that same monomer. In accordance with the invention, the microorganism is capable of depolymerizing said polymer in a manner so as to recover the monomer of interest from it. In the case in which the polymer comprises other monomers, said polymer can be only partially depolymerized so as to liberate the monomer of interest, the other monomers possibly being in the final depolymerization form in the form of oligomers.

In a particular embodiment of the invention, the microorganism is also genetically modified to attenuate at least one pathway for the degradation of an organic monomer which it is capable of synthesizing.

In fact, in some cases, the microorganism of the invention may be naturally capable of using the monomer which it synthesizes as a carbon source for growth thereof. However, these monomers may be of particular industrial interest, in particular for the subsequent synthesis of polymers, and it may be advantageous to prevent their degradation. To this end, in accordance with the invention it is possible to delete all or part of the genes coding for the enzyme or enzymes involved in the degradation of the monomer of interest, using any appropriate recombination/deletion method. It is also possible to attenuate the expression of all or a portion of the genes involved in the degradation of the monomer of interest. To this end, it is, for example, possible to introduce one or more nucleic sequences coding for regulators, such as transcription factors, interfering RNAs, siRNA, etc., which are capable of attenuating the expression of these genes. Similarly, it is possible to modify the promoter sequence of at least one of the genes involved in the degradation of the monomer of interest, so as to attenuate/prevent transcription therein.

In order to prevent the degradation of the synthesized monomers, it is also possible, instead of or as a complement to the above genetic modifications, to regularly enrich the culture medium for the microorganism with substrates which can easily be assimilated by the microorganism, so that it preferentially uses those substrates rather than the synthesized monomer.

The microorganism of the invention may also be genetically modified so as to be able to synthesize a polymer constituted entirely or in part by a monomer which it is capable of synthesizing. As an example, the microorganism may be genetically modified so as to integrate and express a nucleic sequence coding for a particular polymer synthase. Thus, the same microorganism may, in accordance with the invention, produce a monomer with the aid of fermentation and targeted depolymerization of a polymer to be recycled/degraded, and produce a new polymer using the monomers produced. In the case in which the polymer of interest is a heteropolymer, it is possible to enrich the culture medium with the other constituent monomer or monomers of said polymer.

In particular, the invention envisages the depolymerization of aliphatic polyesters such as polylactic acid (PLA), polyhydroxyalkanoates (PHAs), etc., and the synthesis of all or a portion of the associated monomers.

Thus, in a first embodiment, the microorganism of the invention is genetically modified to depolymerize PLA and thus to obtain lactic acid, and concomitantly to synthesize lactic acid from a carbon source.

The enzyme to depolymerize PLA is advantageously selected from a serine protease, a lipase and a PLA depolymerase. Preferably, the enzyme for depolymerizing PLA is selected from the proteinase K from *Tritirachium album*, the lipase A from *Aspergillus niger*, the lipase AY from *Candida rugosa*, the lipase F from *Rhizopus oryzae*, the lipase PS from *Burkholderia* sp. or the lipase cutinase-like enzyme from the S-2 strain of *Cryptococcus* sp. Similarly, the enzyme for the synthesis of lactic acid is advantageously a lactate dehydrogenase. In a particular example, the microorganism is a lactic microorganism, for example a lactic bacterium, naturally excreting a lactate dehydrogenase, i.e., in the wild state.

The invention also provides a method for producing an organic monomer, comprising the steps of:
- contacting a microorganism according to the invention with a carbon source and with a polymer which is capable of being depolymerized by said microorganism, and optionally
- recovering the organic monomer produced.

The organic monomer produced both by fermentation and by depolymerization is advantageously present in the culture medium. It is then possible to treat the culture medium which is enriched in these monomers using any known technique, so as to isolate them and/or to purify them.

In accordance with the invention, it is possible to produce all sorts of monomers, simply by adapting the microorganism used and the genetic modifications introduced. The choice of microorganism as well as the genetic modifications to be provided are within the purview of the skilled person in the light of the teaching of the present application.

The conditions for bringing the microorganism into contact with the carbon source and the polymer, such as the temperature, pH, etc., may be adapted by the skilled person to optimize/favour both production of the monomer by depolymerization of the polymer and production of the monomer by fermentation starting from the carbon source.

The invention also proposes a coculture, for example in a fermenter, of at least two microorganisms, one of which is a genetically modified microorganism of the invention, the second microorganism itself being capable of synthesizing a polymer constituted by at least the monomer produced by the microorganism of the invention.

Thus, the monomer produced by the microorganism of the invention and excreted in the culture medium is used by the second microorganism to produce a polymer of interest which could then be exploited in any type of industry. The method of the invention can thus be used to completely recycle polymers, from their depolymerization into monomers which can be used again, to their re-use in the form of new polymers which can be used in the form of plastics for new applications.

Thus, for example, the microorganism of the invention is a genetically modified lactic bacterium which expresses at least one lactate dehydrogenase and at least one enzyme which is capable of depolymerizing PLA selected from PLA depolymerases, proteases and lipases. This lactic bacterium may be co-cultivated with another microorganism, which may be genetically modified, which can synthesize PLA. Advantageously, the two cocultured microorganisms are selected so that they do not compete for the carbon source, preferably sugars, present in the culture medium. In certain embodiments of the present invention, the term "comprise" can signify "essentially consist of" or "consist of".

EXAMPLES

The invention will be better understood from the examples below, given by way of entirely non-limiting illustration of the invention.

Example 1

Recombinant Lactic Bacterium Expressing a PLA Depolymerase

Method and Apparatus

The cloning techniques used to prepare the recombinant plasmid are those conforming to the techniques described in Sambrook et al., 1989 (*Molecular Cloning: A Laboratory Manual*, Cold Spring Harbor Laboratory Press, Cold Spring Harbor, N.Y.).

The pld gene from *Amycolatopsis* sp. K104-1 with the sequence SEQ ID NO: 1 (Nakamura et al., 2001, Appl. Environ. Microbiol. 67:345-353) is introduced into the plasmid pNZ8048 by homologous recombination (Kuipers et al., 1998, J. Biotechnol. 64:15-21). The recombinant plasmid integrating the pld gene is termed "pNZ-pld".

The wild-type strain *Lactococcus lactis* MG1363 is transformed by the plasmid pNZ-pld introduced into the cell by electroporation using the method described by Ho et al. in 1995 ("Transformation of *Lactococcus* by electroporation", Methods Mol. Biol. 47:195-199). The recombinant bacterium integrating the pNZ-pld plasmid is denoted "MG1363-pNZ-pld". The negative control "MG1363-pNZ8048" corresponds to the wild-type strain *Lactococcus lactis* MG1363 transformed by the empty plasmid pNZ8048.

PLA Depolymerase Activity

The MG1363-pNZ-pld and MG1363-pNZ8048 strains are cultivated in parallel in 2 L fermenters with CDM (Chemically Defined Medium) at 30° C., under anaerobic conditions. Glucose is added to the culture medium to reach a final concentration of 1% (weight/volume), and the pH is kept at 6.5 by automatic addition of NaOH.

The cultures are each divided into two sub-cultures, each batch of two sub-cultures (MG1363-pNZ-pld-1/MG1363-pNZ8048-1 and MG1363-pNZ-pld-2/MG1363-pNZ8048-2) being kept under identical conditions.

Only the second batch (MG1363-pNZ-pld-2/MG1363-pNZ8048-2) receives PLA with a molecular mass of 220,000 Da (Shimadzu Co., Kyoto, Japan), emulsified into the culture medium to 0.1% (weight/volume).

The PLA depolymerase activity is measured after 2 days of culture, by applying the method described in Nakamura et al., 2001 ("Purification and characterization of an extracellular poly(L-lactic-acid) depolymerase from a soil isolate *Amycolatopsis* sp. Strain K104-1", Appl. Environ. Microbiol., 67:345-353).

Culture supernatant from the first batch is removed after two days of culture and analysed by mass spectrometry (Varian Inova 500) in order to evaluate the lactic acid content.

For the two samples (MG1363-pNZ-pld-1 and MG1363-pNZ8048-1), a single peak at 90 Da is observed, corresponding to the lactic acid produced by the bacteria by fermentation. Thus, the recombinant strain MG1363-pNZ-pld is well adapted to producing lactic acid by fermentation of glucose present in the culture medium.

At the same time, culture supernatant from the second batch is removed and analysed by mass spectrometry (Varian Inova 500) in order to evaluate the quantity of lactic acid oligomers (essentially dimers and trimers) present.

For the two samples, (MG1363-pNZ-pld-2 and MG1363-pNZ8048-2), a peak is observed at 220,000 Da, corresponding to PLA present in the culture medium, and a peak at 90 Da, corresponding to lactic acid. Further, for the sample corresponding to the culture medium of MG1363-pNZ-pld-2, the presence of several peaks with an intermediate molecular weight is observed, these peaks being absent for MG1363-pNZ8048-1. These intermediate peaks correspond to lactic acid oligomers of various sizes, which confirms that the PLA of the culture medium has indeed been degraded by the recombinant strain MG1363-pNZ-pld-2.

The recombinant strain MG1363-pNZ-pld, expressing a PLA depolymerase, is indeed capable of producing lactic acid by fermentation and depolymerizing high-molecular-weight PLA present in the culture medium.

Example 2

Evaluation of Lactic Acid Production

The culture supernatants of Example 1, corresponding to batches MG1363-pNZ-pld-1, MG1363-pNZ-pld-2, MG1363-pNZ8048-1 and MG1363-pNZ8048-2, are analysed by HPLC in order to determine the quantity of lactic acid liberated. To this end, an Aminex HPX-87H column, thermostatted at 50° C. and eluted at 0.5 mL/min with a 5 mM sulfuric acid solution, is used for the quantification.

This analysis could demonstrate that the quantity of lactic acid in the supernatant from batch MG1363-pNZ-pld-2 is higher than the quantity of lactic acid in the 3 other conditions (MG1363-pNZ-pld-1, MG1363-pNZ8048-1 and MG1363-pNZ8048-2). Similarly, the presence of a lactic acid dimer is observed only in the culture supernatant from batch MG1363-pNZ-pld-2.

A complementary analysis on a C18 column is carried out using the method described by Vu et al., 2005 ("Oligomer distribution in concentrated lactic acid solutions", Fluid Phase Equilibria, 236:125-135). The analysis of the culture supernatant from batch MG1363-pNZ-pld-2 confirms the presence of lactic acid oligomers up to a degree of polymerization of 6.

Example 3

Culture of *Lactococcus lactis* IL 1403 in the Presence of Proteinase K

The example below deals with the combination of the *Lactococcus lactis* IL 1403 strain and proteinase K for the production of lactic acid. The proteinase K is proteinase K from *Tritirachium album*, available from EUROMEDEX under reference EU0090.

3.1. Selection of the Strain and Culture Medium

The strain used is the *Lactococcus lactis* IL 1403 strain. This strain was cultured on chemically defined medium (CDM medium) supplemented with 5 g/L of glucose and buffered to a pH of 8. A rich medium (containing sources of peptones, proteins or oligopeptides) was not used so as not to include in the culture medium substrates which would be preferred to proteinase K, which could compete with the PLA which is to be degraded.

TABLE 1

Composition of chemically defined medium (CDM) at pH 8

| Compounds | Concentration (g/L) |
|---|---|
| Glucose | 5 |
| Sodium acetate | 1 |
| Ammonium citrate | 0.6 |
| $KH_2PO_4$ | 0.9 |
| $K_2HPO_4$ | 31.2 |
| $MgCl_2 \cdot 6H_2O$ | 0.2 |
| $FeSO_4 \cdot 0H_2O$ | 0.011 |
| $CaCl_2 \cdot 2H_2O$ | 0.05 |
| $ZnSO_4 \cdot 7H_2O$ | 0.005 |
| $COCl_2 \cdot 6H_2O$ | 0.0025 |
| Alanine | 0.24 |
| Arginine | 0.12 |
| Asparagine | 0.34 |
| Glutamine | 0.51 |
| Glycine | 0.17 |

TABLE 1-continued

Composition of chemically defined medium (CDM) at pH 8

| Compounds | Concentration (g/L) |
|---|---|
| Histidine | 0.11 |
| Lysine | 0.35 |
| Methionine | 0.12 |
| Proline | 0.68 |
| Serine | 0.34 |
| Threonine | 0.23 |
| Tryptophan | 0.05 |
| Isoleucine | 0.2 |
| Leucine | 0.47 |
| Valine | 0.33 |
| Phenylalanine | 0.28 |
| Tyrosine | 0.29 |
| Adenine | 0.01 |
| Guanine | 0.01 |
| Uracil | 0.01 |
| Xanthine | 0.01 |
| p-aminobenzoic acid | 0.01 |
| Biotin | 0.01 |
| Cyano-cobalamin (B12) | 0.001 |
| Folic acid | 0.001 |
| Inosine | 0.005 |
| Orotic acid | 0.005 |
| Ca panthotenate | 0.001 |
| Pyridoxamine | 0.005 |
| Pyridoxine (B6) | 0.002 |
| Riboflavin (B2) | 0.001 |
| Thiamine | 0.001 |
| D,L-6,8-thioctic acid | 0.0025 |
| Thymidine | 0.005 |
| Cysteine | 0.17 |

3.2. Selection of Culture Conditions

The aim was to determine the growth rate of *L. lactis* IL 1403 for 4 pH values: 6.6, 7.0, 7.5 and 8.0. The experiments were carried out in tubes containing 15 mL of chemically defined medium with 5 g/L of glucose at 30° C. These experiments were carried out under anaerobic conditions and under aerobic conditions.

Growth was monitored by measuring the optical density at 580 nm for 24 h, and the mean growth rate could be determined.

TABLE 2

Growth parameters for *L. lactis* IL 1403 at different pHs under anaerobic and aerobic conditions

| | anaerobic | | aerobic | |
|---|---|---|---|---|
| IL1403 | $\mu_{mean}$ ($h^{-1}$) | $\mu$ (%) | $\mu_{mean}$ ($h^{-1}$) | $\mu$ (%) |
| 6.6 | 0.52 | 100 | 0.64 | 100 |
| 7.0 | 0.55 | 106 | 0.59 | 93 |
| 7.5 | 0.47 | 90 | 0.59 | 93 |
| 8.0 | 0.36 | 69 | 0.48 | 75 |

While the condition at pH 6.6 corresponds to the reference condition for *L. lactis* IL 1403, the maximum growth rate decreases slightly at pH 7.5, but slightly more at a pH of 8 (25-30%). The aeration conditions had little influence.

These results show that *L. lactis* IL 1403 can be cultured at a pH of 8 with little influence on its growth rate.

3.3. Selection of PLA Depolymerization Conditions

A first study was carried out in order to determine the efficiency of hydrolysis of the proteinase K at different concentrations (1.25, 2.5, 3.75 and 5 g/L) in a chemically defined medium (growth medium for *L. lactis* IL 1403) at 30° C. (growth temperature for lactic bacteria) and a pH of 8 (optimal pH for proteinase K). The concentration of lactic acid liberated after 24 h of hydrolysis was measured by HPLC for 5 initial concentrations of PLA: 2.5, 5, 10, 20 and 40 g/L, and 4 concentrations of proteinase K: 1.25, 2.5, 3.75 and 5 g/L (FIG. 1).

FIG. 1 compares the degradation of PLA to lactic acid in the presence of 4 levels of concentration of proteinase K.

This study shows that after 24 hours, between 27 and 54 mM of lactic acid could be obtained by hydrolysis of PLA by proteinase K in CDM at an initial pH of 8.0. The best hydrolysis yield was obtained for concentrations of PLA and proteinase K of 20 g/L and 3.75 g/L respectively.

3.4. Combination of Lactic Bacteria and PLA Depolymerase

The experiments were carried out in 2 L fermenters (Biostat B plus, Sartorius; 1 L working volume) controlled by a computer. Three culture conditions were tested, starting from a chemically defined medium containing only 2.5 g/L of glucose. The pH was adjusted to a value of 8.0 by adding 10N KOH. The temperature was 30° C. The three conditions are described below:

A. CDM+IL 1403
B. CDM+IL 1403+PLA 20 g/L+Proteinase K (3.75 g/L)
C. CDM+IL 1403+PLA 20 g/L The PLA was autoclaved dry directly in the fermenters. The medium and the proteinase K were added under sterile conditions.

The cultures were monitored kinetically: sampling every two hours, measuring the optical densities at 580 nm, and freezing the culture supernatants after centrifuging for subsequent analysis of the substrate and co-products by HPLC. The correlation between the OD and the dry weight for the *L. lactis* IL 1403 strain is known: 1 g/L=0.3 ODU.

3.4.1. Growth

Figure 2:
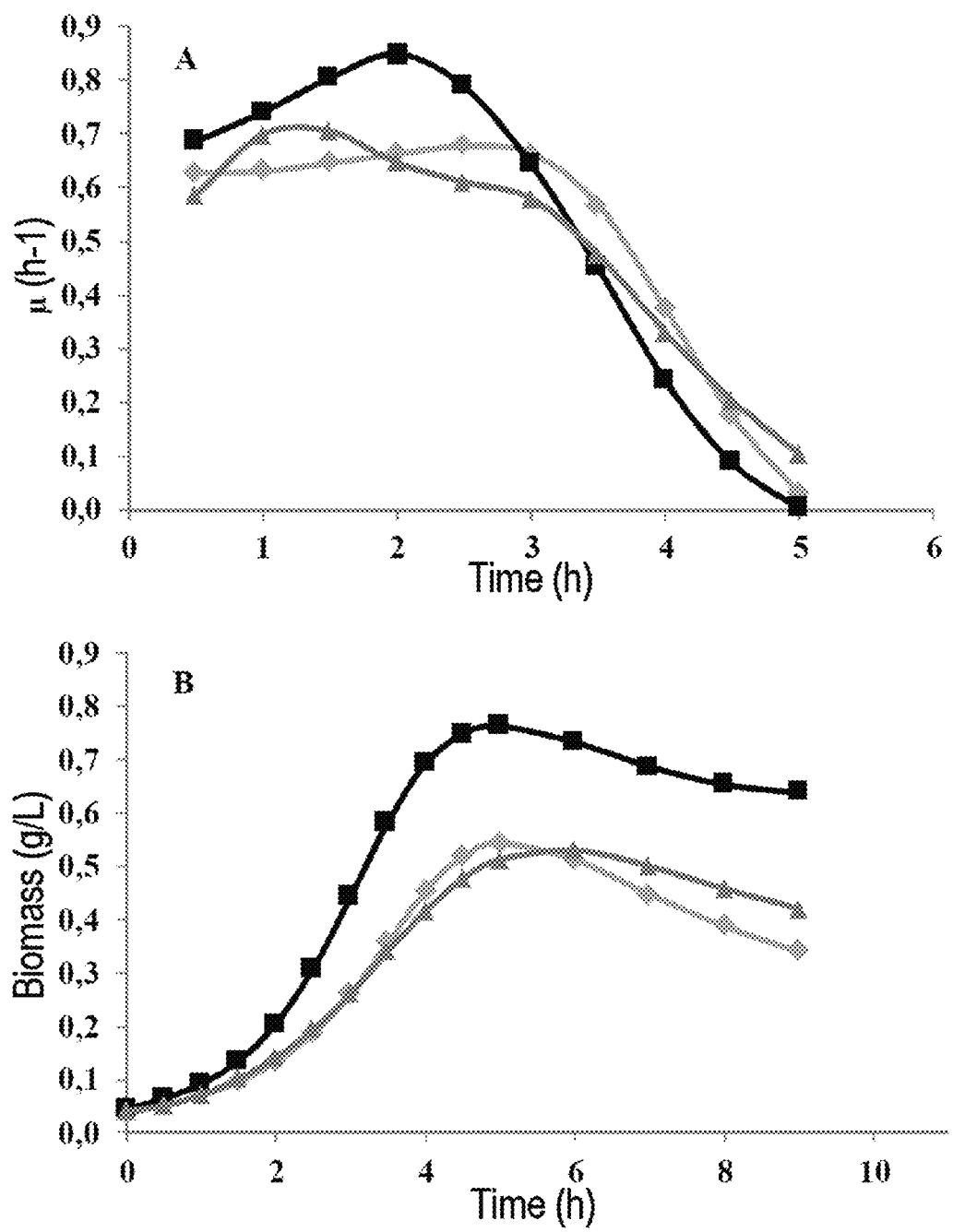
FIG. 2: change in the growth rate (A) and biomass (B) of *L. lactis* IL 1403 in CDM without any additions (✱) with 20 g/L of PLA and 3.75 g/L of proteinase K (■) or with 20 g/L of PLA (▲).

The profiles for the growth rate of *L. lactis* IL 1403 cultured in the absence and in the presence of PLA are similar. The µmax values are 0.65 h$^{-1}$ (no PLA) and 0.70 h$^{-1}$ (with PLA). In contrast, the growth rate profile when proteinase K is added to the medium as a supplement to PLA is very different. The µmax is 0.85 h$^{-1}$ (FIG. 2A). This observation correlates with the biomass monitoring (FIG. 2B). Adding PLA does not modify the production of biomass. We are able to observe practically identical profiles and a maximum biomass of 0.52 and 0.47 g/L, respectively, without or with added PLA. The presence of proteinase K means that a substantially higher maximum biomass of 0.75 g/L could be obtained. This increase in the biomass is not linked to interference with the OD by the hydrolysis of PLA by proteinase K.

Irrespective of the medium conditions, growth stops after 4h30 of culture and corresponds to complete consumption of the glucose.

3.4.2. Catabolic Balance

The various culture conditions for *L. lactis* IL 1403 were monitored dynamically over 9 hours, then two final samples were taken at 15 hours and 24 hours.

Figure 3:
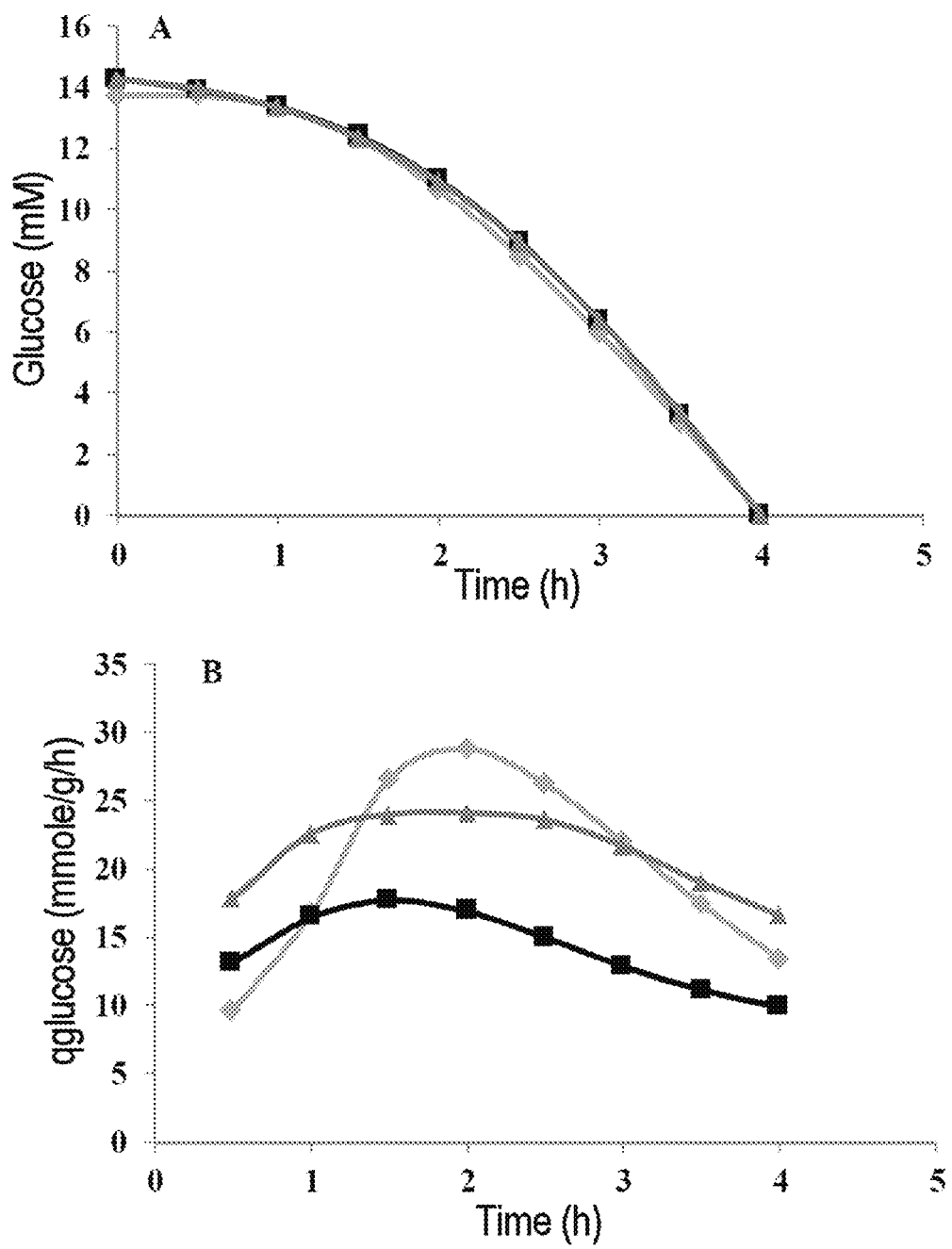
FIG. 3: change in the concentrations of glucose (A) and specific glucose consumption rates (B) for *L. lactis* IL 1403 in CDM without any additions (✱) with 20 g/L of PLA and 3.75 g/L of proteinase K (■) or with 20 g/L of PLA (▲).

The change in the concentrations of glucose in the culture medium is strictly similar under the three culture conditions. The glucose is completely consumed after 4 h of culture (FIG. 3A). Regarding the specific glucose consumption rates during the exponential growth phase (1h-3h), they are very close in the medium without PLA and with PLA. The maximum values for the specific glucose consumption rates (qglucose) are respectively 27 and 24 mmole/g/h. When proteinase K is added to the medium, this qglucose is only 17 mmole/g/h. This difference in qglucose is in agreement with a higher biomass in the fermenter containing proteinase K.

Figure 4:
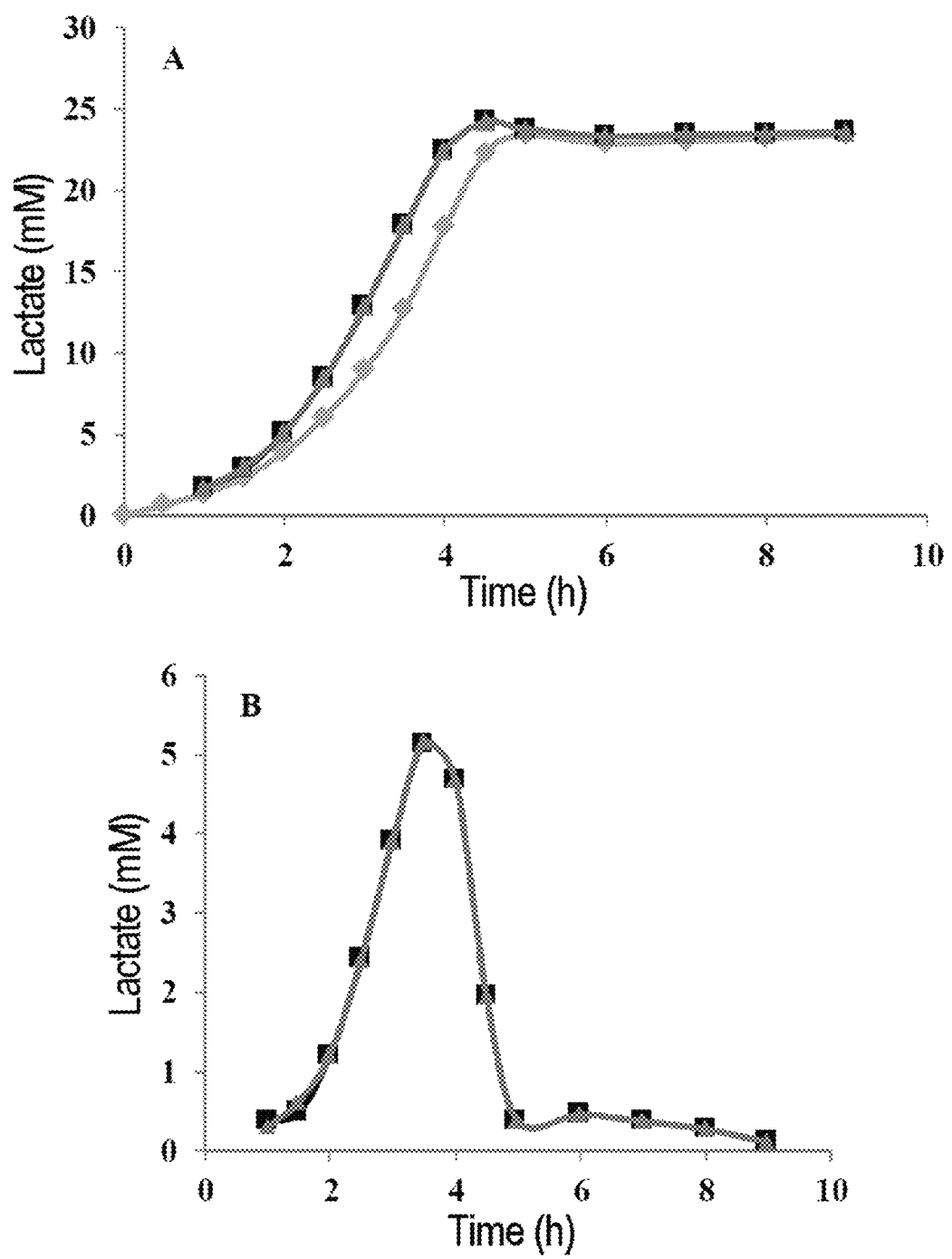
FIG. 4: change in the concentrations of lactate (A) for *L. lactis* IL 1403 in CDM without any additions (✱), with 20 g/L of PLA and 3.5 g/L of proteinase K (■) or with 20 g/L of PLA (▲) and calculation of lactate differential (B) between the condition without PLA and the conditions with PLA.
Figure 5:
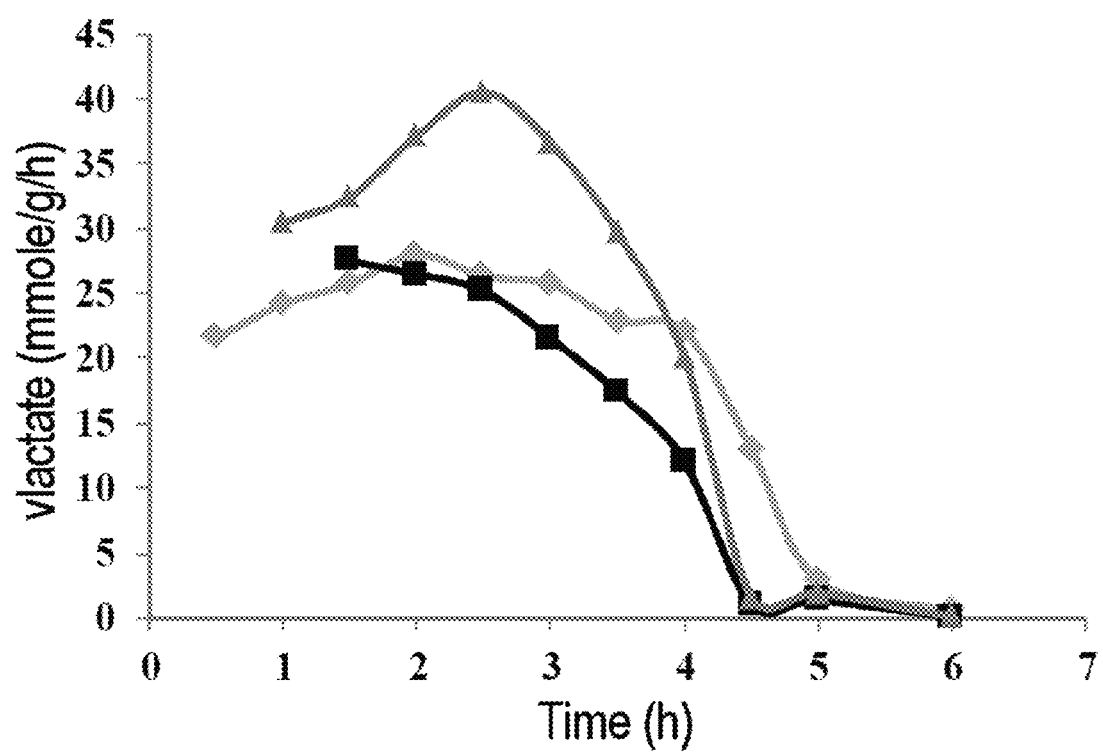
FIG. 5: change in the specific production rates of lactate for *L. lactis* IL 1403 in CDM without any additions (✱) with 20 g/L of PLA and 3.75 g/L of proteinase K (■) or with 20 g/L of PLA (▲).

The lactate is the major fermentation product. Adding PLA and proteinase K does not modify the homolactic nature of the strain in any way. More than 90% of the pyruvate stream leads to the production of lactic acid, while less than 7% is directed towards the production of acetic acid. The catabolic carbon balances are equilibrated between 89% and 95%, taking into account the $CO_2$ theoretically produced by the metabolism. The overall stoichiometric balances in mM of carbon, calculated after 24 h of culture, are as follows:

IL 1403
  0-24 h: 14.2 Glucose→24.7 Lactate+2.1 Acetate+2.1 $CO_2$
IL 1403 with PLA
  0-24 h: 14.3 Glucose→23.8 Lactate+1.5 Acetate+1.5 $CO_2$
IL 1403 with PLA and proteinase K
  0-24 h: 14.3 Glucose→23.8 Lactate+1.5 Acetate+1.5 $CO_2$ Overall, the change in the lactate concentrations followed the same profile in the three culture conditions, though with slight differences in the onset of culture when PLA is present with or without proteinase K (FIG. 4A). In fact, the PLA has been autoclaved, possibly causing thermal fragilization or autohydrolysis. This difference in concentration (less than 5 mM, see FIG. 4B) with respect to the condition with no added PLA is not very significant. It is also rigorously identical in the presence or otherwise of proteinase K and thus could not in any case be attributed to the hydrolysis of PLA by proteinase K. As regards the specific lactate production rates (FIG. 5), no major difference between the three conditions is observed.

3.5. Conclusion

In the tests carried out in a regulated pH fermenter, the degradation of PLA to lactic acid by proteinase K could not be detected. The production of lactate could be considered to derive exclusively from the consumption of glucose: 1.66 to 1.74 mmole of lactate produced per mmole of glucose, the value normally encountered with this strain.

This demonstrates that simply adding PLA-depolymerase to a culture of lactic bacteria cannot increase the lactic acid produced by this method.

Example 4

Recombinant Strain for the Production of Succinate 4.1. Construction of an *Escherichia coli* Strain Expressing a PBS-Depolymerase A strain of *Escherichia coli*, SBS 550 MG-PHL413, expressing a PBS-depolymerase (cutinase-like enzyme (CLE) from *Cryptococcus* sp. S-2) is constructed. The gene sequence for the CLE is presented in SEQ ID NO: 2; the corresponding amino acid sequence is presented in SEQ ID NO: 3.

To this end, the gene for the CLE is amplified by PCR starting from genomic DNA of the strain *Cryptococcus* sp. S-2 (Masaki et al., 2005: Kazuo Masaki, Numbi Ramudu Kamini, Hiroko Ikeda, and Haruyuki Iefuji, "Cutinase-Like Enzyme from the Yeast *Cryptococcus* sp. Strain S-2 Hydrolyzes Polylactic Acid and Other Biodegradable Plastics", AEM, 71:7548-7550).

The following primers are used:
sense primer carrying a BamHI restriction site:

```
                                             (SEQ ID NO: 6)
        GATCGGATCCGCCACGTCCAGCGCTTGTCCG
``` anti-sense primer carrying a XhoI restriction site:

```
                                             (SEQ ID NO: 7)
        CCGGAACTCGAGGGCCGACCCGCCAAGCTTGTTG
```

At the same time, the vector pET26b(+) (Novagen) is linearized by digestion with the restriction enzymes BamHI and XhoI.

The insert and the linearized vector are purified on gel using the QIAquick Gel Extraction kit (Qiagen). A ligation is carried out with ligase T4 (T4 DNA ligase, New England Biolabs). The ligation product is transformed in *E. coli* DH5a, then spread onto LB-Agar medium containing 40 μg/mL of kanamycin. After leaving overnight at 37° C., one colony is removed and cultured in 5 mL of LB medium containing 40 μg/mL of kanamycin at 37° C. overnight (16 to 18 h). The amplified vector is purified using the QIAprep Spin Miniprep Kit (Qiagen) and verified by sequencing.

The vector obtained thereby is denoted pET26b-CLE.

The vector pET26b-CLE is transformed in the *E. coli* SBS 550 MG-PHL413 strain (Sanchez et al., 2005: Ailen M. Sanchez, George N. Bennett, Ka-Yiu San, "Novel pathway engineering design of the anaerobic central metabolic pathway in *Escherichia coli* to increase succinate yield and productivity", Metabolic Engineering, 2005, 7:229-239). A negative control is constructed by transformation of the empty vector pET26b in *E. coli* SBS 550 MG-PHL413. The two strains obtained thereby are respectively denoted *E. coli* SBS 550 MG-CLE and *E. coli* SBS 550 MG pET26b.

4.2. Production of Succinic Acid by Culture of the Strain *E. coli* SBS 550 MG-CLE The strains *E. coli* SBS 550 MG-CLE and *E. coli* SBS 550 MG pET26b are cultured in a 2 L fermenter in a mineral medium supplemented with 20 g/L of glucose and 20 g/L of PBS (Bionolle 1001, Showa Highpolymer Corp. Ltd., Tokyo, Japan) micronised to 500 μm. The temperature is maintained at 37° C. and the pH at 6.5 by adding KOH. A first culture phase under aerobic conditions produces biomass. When the optical density at 600 nm reaches 0.6, a solution of IPTG is added to each fermenter in order to obtain a final concentration of 1 mM and to induce the production of PBS-depolymerase in the fermenter, corresponding to the culture of the strain *E. coli* SBS 550 MG-CLE. Culture is continued under anaerobic conditions by continuously injecting 0.4 vvm of $CO_2$ until all of the glucose has been consumed.

Samples are taken from the culture medium at regular intervals in order to measure the bacterial growth and to analyse the composition of the supernatant. The glucose concentration and the succinic acid production are measured by HPLC on a Bio-Rad HPX 87H column. Detection is carried out by refractometry.

During fermentation, glucose is indeed consumed by each of the strains and succinic acid is produced. The fermenter corresponding to the culture of the strain *E. coli* SBS 550 MG-CLE exhibits a higher production of succinic acid, corresponding to the depolymerization of PBS by the CLE (PBS-depolymerase) expressed by the strain *E. coli* SBS 550 MG-CLE.

Example 5

Recombinant Strain for the Production of 1,3-Propanediol 5.1. Construction of a Strain of *Clostridium acetobutylicum* Expressing a PTT-Depolymerase.

The gene Bta1 corresponding to cutinase TfH is amplified from genomic DNA obtained from the strain *Thermobifida fusca* DSM 43793. The sequence of the Bta1 gene of the cutinase TfH is presented in SEQ ID NO: 4; the corresponding amino acid sequence is presented in SEQ ID NO: 5. At the same time, the signal peptide PS-Ce148A of the cellulase from *Clostridium acetobutylicum* ATCC 824 (Ce148A: Sabathé, F., A. Belaich, and P. Soucaille, 2002, "Characterization of the cellulolytic complex (cellulosome) of *Clostridium acetobutylicum*", FEMS Microbiol. Lett., 217: 15-22) was amplified by PCR (polymerase chain reaction).

The expression vector pSOS952 (Perret, S., Casalot, L., Fierobe, H. P., Tardif, C., Sabathe, F., Belaich, J. P., and Belaich, A., 2004, "Production of heterologous and chimeric scaffoldins by *Clostridium acetobutylicum* ATCC 824", J. Bacteriol., 186:253-257) is linearized by digestion with the restriction enzymes BamHI and Nar I.

Finally, the above gene bta1 of the signal peptide PS-Ce148A is cloned into the linearized vector using the In-Fusion cloning kit (In-Fusion® HD Cloning Kit, Clontech). The vector obtained thereby is denoted pSOS952-bta1.

The vector pSOS952-bta1 is transformed in *E. coli* ER2275 (pAN1) so that it could be methylated by the methyltransferase φ3T I using the method described by Mermelstein and Papoutsakis, 1993 and Green et al., 1996. After purification, the plasmid is transformed by electroporation in the strain *Clostridium acetobutylicum* DG1 (pSPD5) (Gonzalez et al., 2005). The recombinant strain obtained is denoted *C. acetobutylicum* DG1-pSOS952-bta1.

A control strain (negative control) is constructed by transformation of the vector pSOS952 in *Clostridium acetobutylicum* DG1 (pSPD5).

5.2. Production of 1,3-Propanediol by Culture of the Strain *C. acetobutylicum* DG1-pSOS952-bta1

A pre-culture of the two strains obtained thereby is carried out at 35° C. on a synthetic medium containing 10 g/L of glycerol as the carbon source and under anaerobic conditions (sealed flask and in nitrogen, Gonzalez et al., 2005). Each pre-culture is used to seed a 250 mL fermenter so as to have an absorbance at 600 nm equal to 0.05 at t0. The culture medium is constituted by the synthetic medium described by Gonzalez et al., 2005, supplemented with 50 g/L glycerol and PTT (polytrimethylene terephthalate, Sorona, micronised to 500 μm, DuPont) and kept under anaerobic conditions under a nitrogen atmosphere. The pH of the fermenter is kept at 6.5 by adding $NH_4OH$.

Samples of the culture medium are taken at regular intervals in order to measure the bacterial growth and to analyse the composition of the supernatant. The concentration of glycerol and the production of 1,3-propanediol are measured by means of HPLC on a Bio-Rad HPX 97H column. Refractometry is used for detection.

During the fermentation, the glycerol is indeed consumed by each of the strains and 1,3-propanediol and acetate are produced. The fermenter corresponding to the culture of the strain *C. acetobutylicum* DG1-pSOS952-bta1 exhibits a greater production of 1,3 propanediol as well as the production of terephthalic acid, which corresponds to depolymerization of PTT by PTT-depolymerase secreted into the culture medium.

The invention claimed is:

1. A genetically modified microorganism which is genetically modified so as to:
   i) synthesize a lactic acid monomer by fermentation of a carbon source, and
   ii) depolymerize a polylactic acid polymer (PLA);
   wherein the microorganism is transformed with at least one nucleic acid encoding an enzyme for depolymerizing PLA and at least one nucleic acid encoding a lactate dehydrogenase for synthesizing lactic acid monomers.

2. The microorganism according to claim 1, expressing at least one enzyme for depolymerizing PLA selected from a proteinase K, a lipase and a PLA depolymerase.

3. The microorganism according to claim 1, in which said microorganism is a lactic bacterium.

4. The microorganism according to claim 2, in which said microorganism is a lactic bacterium.

5. A method for producing a lactic acid monomer, comprising the step of:
   contacting a microorganism according to claim 1 with a carbon source and with a PLA.

6. The method for producing a lactic acid monomer according to claim 5 further comprising the step of recovering the lactic acid produced.

7. A coculture of microorganisms comprising at least a first microorganism according to claim 1 and at least a second microorganism, which is capable of synthesizing a PLA comprising lactic acid produced by the first microorganism.

8. A method for synthesizing polymers comprising the step of contacting a coculture of microorganisms according to claim 7 with a carbon source and with a PLA which is capable of being degraded by the first microorganism.

9. The method for synthesizing polymers according to claim 8, further comprising the step of recovering polymer produced by the second microorganism.

10. The method according to claim 9, in which the second microorganism is genetically modified to synthesize PLA starting from said lactic acid monomers.

11. The microorganism according to claim 1, in which said microorganism is a lactic bacterium and wherein the microorganism is transformed with at least one nucleic acid encoding a proteinase K for depolymerizing PLA.

* * * * *

UNITED STATES PATENT AND TRADEMARK OFFICE
CERTIFICATE OF CORRECTION

PATENT NO. : 9,476,073 B2
APPLICATION NO. : 14/387285
DATED : October 25, 2016
INVENTOR(S) : Cédric Boisart Page 1 of 1

It is certified that error appears in the above-identified patent and that said Letters Patent is hereby corrected as shown below:

In the Specification

Column 3,
Line 22, "( * )," should read --( * ),'--.
Line 27, "( * )," should read --( * ),'--.
Line 36, "( * )," should read --( * ),'--.

Column 5,
Line 17, "(PB SA)" should read --(PBSA)--.

Signed and Sealed this
Seventh Day of March, 2017

Michelle K. Lee
*Director of the United States Patent and Trademark Office*

SEQUENCE LISTING

<160> NUMBER OF SEQ ID NOS: 7

<210> SEQ ID NO 1
<211> LENGTH: 717
<212> TYPE: DNA
<213> ORGANISM: Amycolatopsis sp. K104-1

<400> SEQUENCE: 1

| | | | | | | |
|---|---|---|---|---|---|---|
| gtgaaattcg | gcaagttcgt | cctgctggcc | gcgagcaccg | cactggccgt | cgtcggcctc | 60 |
| ggcggtccgg | cggccgccga | cagcaccccg | caggcccagc | cgtcgatcat | cggtggcagc | 120 |
| aacgccacca | gtggcccctg | gcggccccgg | ctgttcgtca | acggccggca | gaactgcacc | 180 |
| gcgacgatca | tcgccccgca | gtacatcctc | accgccaagc | actgcgtcag | cagctccggc | 240 |
| acctacacgt | tccgcatcgg | cagcctggac | cagacgagcg | gcggcacgat | ggccaccggc | 300 |
| tccacgatca | cgcgctaccc | gggctccgcc | gacctggcga | tcgtccggct | caccacctcg | 360 |
| gtgaacgcca | cctactcgcc | actcggcagc | gtcggtgacg | tttcggtcgg | ccagaacgtc | 420 |
| tcggtctacg | gctggggcgc | gaccagccag | tgcggctccg | agatcaactg | ccagtcgcgg | 480 |
| tacctgaagg | tcgcgacggt | gcgggtgaac | tcgatcagct | gcagcgacta | caccggcggc | 540 |
| gtcgccgtgt | gcgcgaaccg | cgtcaacggc | atcaccgccg | gcggcgactc | cggcggcccg | 600 |
| atgttcgctt | ccgccgcca | ggtcggcgtc | gcgtcgacca | cgaccggggt | gaacaacacg | 660 |
| gcgtacacca | acatcacgcg | ttatcgcagc | tggatttcgc | aggtggcggg | cgtctga | 717 |

<210> SEQ ID NO 2
<211> LENGTH: 1881
<212> TYPE: DNA
<213> ORGANISM: Cryptococcus sp. S-2
<220> FEATURE:
<221> NAME/KEY: misc_feature
<222> LOCATION: (1004)..(1594)
<220> FEATURE:
<221> NAME/KEY: misc_feature
<222> LOCATION: (1642)..(1770)

<400> SEQUENCE: 2

| | | | | | | |
|---|---|---|---|---|---|---|
| gctggcctcg | gcgtagcaaa | ggcgatgcgg | acgatccacg | gcgaggccta | ccagtccggc | 60 |
| caggcctgtg | atctgacgta | tcggtgagtt | gctggacgat | cgtataccgg | cactgagctg | 120 |
| acggcgtcta | gcgctcccgg | agacgccatc | gactacgcct | acggcgtcac | tgacatccgg | 180 |
| tggtcgtatt | ccgccgaact | gcgagatacc | ggcacagtga | gttgggctgt | gacgcctgca | 240 |
| taccccctaca | gaagctgatc | cgcggtcagt | acggcttcat | gcttcccccg | tcattaatcc | 300 |
| gatcggctgc | ggaggagacc | acggccggac | tgatgtacct | gggcaaattc | atctacaacc | 360 |
| tcgagatagc | cggctaagcc | gccaatgatg | ggcccggaag | gcacctgtcc | tcgtgtgacg | 420 |
| ctagtgatga | aaatgtaccg | atgtatttta | cttattctac | cgcgatgagg | agctccgttc | 480 |
| gatccagact | atcggtacag | tcctgtcatg | tgatgagact | gcggttagtg | ccggtgaata | 540 |
| tgccaggtcc | cacttcgcgc | ggtactagtt | acagtagtag | tctggactct | gccgagctcg | 600 |
| cttaacagca | acattactgg | gcgtcgtgcc | tgtgcacctg | atcctgttta | gcgtcttccg | 660 |
| gttatgtcgg | gatgaagtcg | ttctcggacc | cattttttgaa | cgaatggcgc | cagagctgag | 720 |
| gcgtggactc | ggagcatatg | caagatgtag | gaggccatct | gactgttgat | tgatcggggg | 780 |
| acgggggaat | ggcctgccga | gagaaacaca | ggtctagcgg | tgattgggac | gagcggtggc | 840 |
| gtgagactag | cctggaatat | cgggtgaatc | aggtcctgac | ttcgccgggt | ggcaggatag | 900 |
| caggtgccgg | cttatcagat | ataagaaggg | gtcatgcccc | aataccagcg | acgacccact | 960 |

```
cacctctccg agccataccg cacacccccca gctcccgtca gacatgctcg tctccgctct    1020
cgctctcgcg gtgctgtccg ctgcttctct cggccgagcc gcaccaacgc ccgagtccgc    1080
cgaggcgcac gagctcgagg cccgcgccac gtccagcgct tgtccgcagt acgtcctgat    1140
caacacgcga ggcacgggcg agccgcaagg ccagtcggcc ggcttccgaa cgatgaacag    1200
ccagatcacc gccgcgctgt cgggtggcac catctacaac actgtctaca ccgccgattt    1260
cagccagaac agcgcggccg gcacggccga catcatccgc cggatcaact cgggtctcgc    1320
ggccaacccg aacgtgtgct acatcctcca agggtacagc cagggcgcgg ctgctaccgt    1380
cgtcgcgctg caacagctcg gcacgagtgg agcggcgttc aacgccgtca agggtgtgtt    1440
cctcattggc aacccggacc acaagtcggg cctgacttgc aacgtcgact cgaacggcgg    1500
cactaccaca cgcaatgtca acggcctgtc ggtcgcgtac cagggctcgg tcccctcagg    1560
atgggtcagc aagactctcg atgtctgcgc ttatgtacgt gcacgctgct catgatttga    1620
ggacaagcgc tgacccggta gggcgacggc gtgtgcgaca ccgcgcacgg attcggtatc    1680
aacgcacagc acctgtcgta ccctagtgac caaggcgtcc agaccatggg atacaagttt    1740
gccgtcaaca agcttggcgg gtcggcctaa acggcactct tcgacctcga ttagttcaga    1800
gactgaggca gttgtgatcg ctccggctgc tagggagtgg accagtatca cgtttacata    1860
tgcacattat atctcgctag c                                              1881
```

```
<210> SEQ ID NO 3
<211> LENGTH: 239
<212> TYPE: PRT
<213> ORGANISM: Cryptococcus sp. S-2

<400> SEQUENCE: 3

Met Leu Val Ser Ala Leu Ala Leu Ala Val Leu Ser Ala Ala Ser Leu
1               5                   10                  15

Gly Arg Ala Ala Pro Thr Pro Glu Ser Ala Glu Ala His Glu Leu Glu
            20                  25                  30

Ala Arg Ala Thr Ser Ser Ala Cys Pro Gln Tyr Val Leu Ile Asn Thr
        35                  40                  45

Arg Gly Thr Gly Glu Pro Gln Gly Gln Ser Ala Gly Phe Arg Thr Met
    50                  55                  60

Asn Ser Gln Ile Thr Ala Ala Leu Ser Gly Gly Thr Ile Tyr Asn Thr
65                  70                  75                  80

Val Tyr Thr Ala Asp Phe Ser Gln Asn Ser Ala Gly Thr Ala Asp
                85                  90                  95

Ile Ile Arg Arg Ile Asn Ser Gly Leu Ala Ala Asn Pro Asn Val Cys
                100                 105                 110

Tyr Ile Leu Gln Gly Tyr Ser Gln Gly Ala Ala Ala Thr Val Val Ala
            115                 120                 125

Leu Gln Gln Leu Gly Thr Ser Gly Ala Ala Phe Asn Ala Val Lys Gly
        130                 135                 140

Val Phe Leu Ile Gly Asn Pro Asp His Lys Ser Gly Leu Thr Cys Asn
145                 150                 155                 160

Val Asp Ser Asn Gly Gly Thr Thr Thr Arg Asn Val Asn Gly Leu Ser
                165                 170                 175

Val Ala Tyr Gln Gly Ser Val Pro Ser Gly Trp Val Ser Lys Thr Leu
            180                 185                 190

Asp Val Cys Ala Tyr Gly Asp Gly Val Cys Asp Thr Ala His Gly Phe
        195                 200                 205
```

```
Gly Ile Asn Ala Gln His Leu Ser Tyr Pro Ser Asp Gln Gly Val Gln
    210                 215                 220

Thr Met Gly Tyr Lys Phe Ala Val Asn Lys Leu Gly Gly Ser Ala
225                 230                 235

<210> SEQ ID NO 4
<211> LENGTH: 4451
<212> TYPE: DNA
<213> ORGANISM: Thermobifida fusca
<220> FEATURE:
<221> NAME/KEY: CDS
<222> LOCATION: (2027)..(2932)

<400> SEQUENCE: 4
```

| | | | | | |
|---|---|---|---|---|---|
| acgtgtcctc | tgcactgcaa | tccccgcttc | ccagcgcatc | accggccccg | gcgcgggccg | 60 |
| gacgcggcgg | ggtgctcccc | gcgcccggct | gggttgtggg | tgcggtctgc | acgtgttcg | 120 |
| ccgtcgcggg | cctcaccctg | gtcccgccgt | ggctgggcct | gggatgggac | gaggtcgtct | 180 |
| acgtcagcca | gtacgatccc | cgcaatcccg | ccgcgttctt | cagcgcgccc | cggtcgcgcg | 240 |
| gggtgtcgct | gctggccgcg | ccggtggtgc | tcgtcaccga | ctcggtggtg | gcgcttcggg | 300 |
| tgtggctggc | tgcggccgcg | gccgtggcca | tgggcgcggc | gttctggccg | tggctgcggc | 360 |
| tgtatccgcg | cagcggggtg | gtgccgctcg | cagccttcgg | gtatgcgagc | ctgtgggtca | 420 |
| gcttgttcta | cgcggccgcg | gcgatgccca | accatttcac | ggcgatggcc | gcggtgggcg | 480 |
| cggtcggctg | gttcctggtc | gcggtccgcg | aacccgcgtc | ccggtctgcg | ctggccgggc | 540 |
| ttgcagccat | gctggcggtg | gccgggctga | tgccgcccag | tgacgcgttc | tggttgaccg | 600 |
| cgcctttggg | gctggccgga | cttgtcgtgc | cgtcgtggcg | gcgggtaccg | ctgctcgcgg | 660 |
| ccgtggccgg | cggcggcctg | gccggtgtgg | caccgtggct | ggtggaagcg | gagctctcct | 720 |
| acgggggcgt | gctctcccgg | ctggctcggg | cctccgagat | ccagggcggg | accgggtgga | 780 |
| ccctggctgt | ggggtacgtg | gtcaccgcgt | tggacgggcc | gctgctgtgc | cgcccctgca | 840 |
| ccgaggacct | ggtgcgctgg | cctgccctgc | tctggccgat | cgctttggtc | gtactggtgg | 900 |
| tgggcgggat | tgtcggcgct | caccgggcgg | gacgtcccgc | tctggggtgg | ctgcctgtgg | 960 |
| tggtcgccgg | gtcgctcgcg | ttcacctacc | tgttcctcgt | ctcctacacg | gcgccgcgtt | 1020 |
| tcctccagcc | cacgtacgcg | ctgctcatgc | tgcccgctgc | ggcaggactg | cacgatgcgt | 1080 |
| ggacggcgac | ccggccccgg | ctgcgtcccg | tgctgggtgc | cgggttggcc | gtggcgatcc | 1140 |
| tcggacatct | cctcatccag | ggggcgatcc | tcacccactg | ggtcaccgtc | cacacggcgg | 1200 |
| cccgggagaa | ctatgcccgg | ctcgccgagg | agctgcatgc | ggccgggcta | cgcccgccgt | 1260 |
| gcgtgctcac | cggggacgag | gccattccca | tcgcctacta | cgcggggtgc | gcctcggcgg | 1320 |
| cggcgtccgg | caacaacacc | acgcacaccc | tggaggagct | gctcgcggtg | agccggaccg | 1380 |
| taccgttcgg | gctgctcgcc | aaggaggacg | tccgcccga | gtgggccgct | gactgggacg | 1440 |
| cgctgcccgt | gggtccgcc | gacgaccgt | ggtcgtgggt | ggtgtacctc | ccgccgtgga | 1500 |
| gcccgctgtc | cattccggaa | tgagtccgag | cgggtattct | cgctacctat | ttcagccccg | 1560 |
| gagtcaggat | tccgggcttt | ttctctgtcc | caccccaccc | ccacatttat | ggacatttcc | 1620 |
| tcgcaaaaca | cactatttga | cctgtggttt | ggcgagacac | tggtgatttc | acggatgcca | 1680 |
| tccggctccc | ccatgccgaa | tagtgacgtt | gcggttaaga | cacagaaccg | gttaccgccg | 1740 |
| gatctcctta | ccgcaacgtt | gtgagcggcc | taccgcaatg | gctgaccacg | acgaggcaga | 1800 |
| ccctcgccca | ccagtgcctg | ccgcatcggc | ccccgctgc | gacggtcacg | cccggcttcg | 1860 |

```
gactctcggg gacggcgccc cggtgggcat ggaccgttca gtgtcccac ggtgaacggc    1920 ccaccatccc ccgcacatcc ggtctgcccc taccgtggcc agtgccgctc ctccctccgt    1980
ccacgggcga ccctccgctt cgcccttac acgaagagga tgtgca atg gct gtg       2035
                                                 Met Ala Val
                                                   1 atg acc ccc cgc cgg gag cgc tct tcc ctg ctc tcc cga gct ctg caa     2083
Met Thr Pro Arg Arg Glu Arg Ser Ser Leu Leu Ser Arg Ala Leu Gln
      5               10                  15 gtg acg gct gcg gct gcc aca gcg ctt gtg acc gcg gtc agc ctg gcc     2131
Val Thr Ala Ala Ala Ala Thr Ala Leu Val Thr Ala Val Ser Leu Ala
 20                  25                  30                  35 gcc ccc gct cat gcc gcc aac ccc tac gag cgc ggc ccc aac ccg acc     2179
Ala Pro Ala His Ala Ala Asn Pro Tyr Glu Arg Gly Pro Asn Pro Thr
                 40                  45                  50 gac gcc ctg ctc gaa gcc agc agc ggc ccc ttc tcc gtc agc gag gag     2227
Asp Ala Leu Leu Glu Ala Ser Ser Gly Pro Phe Ser Val Ser Glu Glu
             55                  60                  65 aac gtc tcc cgg ttg agc gcc agc ggc ttc ggc ggc ggc acc atc tac     2275
Asn Val Ser Arg Leu Ser Ala Ser Gly Phe Gly Gly Gly Thr Ile Tyr
         70                  75                  80 tac ccg cgg gag aac aac acc tac ggt gcg gtg gcg atc tcc ccc ggc     2323
Tyr Pro Arg Glu Asn Asn Thr Tyr Gly Ala Val Ala Ile Ser Pro Gly
     85                  90                  95 tac acc ggc act gag gct tcc atc gcc tgg ctg ggc gag cgc atc gcc     2371
Tyr Thr Gly Thr Glu Ala Ser Ile Ala Trp Leu Gly Glu Arg Ile Ala
100                 105                 110                 115 tcc cac ggc ttc gtc gtc atc acc atc gac acc atc acc acc ctc gac     2419
Ser His Gly Phe Val Val Ile Thr Ile Asp Thr Ile Thr Thr Leu Asp
                 120                 125                 130 cag ccg gac agc cgg gca gag cag ctc aac gcc gcg ctg aac cac atg     2467
Gln Pro Asp Ser Arg Ala Glu Gln Leu Asn Ala Ala Leu Asn His Met
             135                 140                 145 atc aac cgg gcg tcc tcc acg gtg cgc agc cgg atc gac agc agc cga     2515
Ile Asn Arg Ala Ser Ser Thr Val Arg Ser Arg Ile Asp Ser Ser Arg
         150                 155                 160 ctg gcg gtc atg ggc cac tcc atg ggc ggc ggc ggc acc ctg cgt ctg     2563
Leu Ala Val Met Gly His Ser Met Gly Gly Gly Gly Thr Leu Arg Leu
    165                 170                 175 gcc tcc cag cgt ccc gac ctg aag gcc gcc atc ccg ctc acc ccg tgg     2611
Ala Ser Gln Arg Pro Asp Leu Lys Ala Ala Ile Pro Leu Thr Pro Trp
180                 185                 190                 195 cac ctc aac aag aac tgg agc agc gtc acc gtg ccg acg ctg atc atc     2659
His Leu Asn Lys Asn Trp Ser Ser Val Thr Val Pro Thr Leu Ile Ile
                 200                 205                 210 ggg gcc gac ctc gac aca atc gcg ccg gtc gcc acg cac gcg aaa ccg     2707
Gly Ala Asp Leu Asp Thr Ile Ala Pro Val Ala Thr His Ala Lys Pro
             215                 220                 225 ttc tac aac agc ctg ccg agc tcc atc agc aag gcc tac ctg gag ctg     2755
Phe Tyr Asn Ser Leu Pro Ser Ser Ile Ser Lys Ala Tyr Leu Glu Leu
         230                 235                 240 gac ggc gca acc cac ttc gcc ccg aac atc ccc aac aag atc atc ggc     2803
Asp Gly Ala Thr His Phe Ala Pro Asn Ile Pro Asn Lys Ile Ile Gly
245                 250                 255 aag tac agc gtc gcc tgg ctc aag cgg ttc gtc gac aac gac acc cgc     2851
Lys Tyr Ser Val Ala Trp Leu Lys Arg Phe Val Asp Asn Asp Thr Arg
                 260                 265                 270                 275 tac acc cag ttc ctc tgc ccc gga ccg cgc gac gga ctc ttc ggc gag     2899
Tyr Thr Gln Phe Leu Cys Pro Gly Pro Arg Asp Gly Leu Phe Gly Glu
```

```
                  280                 285                 290
gtc gaa gag tac cgc tcc acc tgc ccg ttc tag gaagagaaca cgacgagtct    2952
Val Glu Glu Tyr Arg Ser Thr Cys Pro Phe
            295                 300 ttcctcccca ttctttcggt ggcggtcact gcggtggccg ccaccggccg ttttgtcccc    3012
ccttttcatt cgaaaaatgc gacaaaccac ccttttttgcc ccatcgcacc cccgataccg   3072
aacgaagttc gggtacaaca ctggtggttt tacggatgca tgatcactgt gacttgcccc    3132
atagtggcaa cgcagtcgag ataaggagcg cataaacccc aaacctcctt acctccgcct    3192
gctgagcggc tcgttgaccg cacgtggccg ggcacaccgg cttcgcctac cggtcgcacg    3252
cgccgtgcct tctccacccc cgcggcggaa aggcgcggcg ctcgcgggct ggaccgttcg    3312
gaccccacgc gaacggcccg gaacccatgg caccccccgcg tccgggaggc aagcgccgcg   3372
tgcctaccgc caacggcgcc gctcacctcc agtggcgagg cgggagtccg ggtccacgtc    3432
catgcatgcc cccgcatgcg gcgcggcccg gccctgcaca gaaccgaaga ggacgtgcaa    3492
tggctgtgat gacccccgc cgggagcgct cttccctgct ctcccgggca ctgcgcttca    3552
ccgccgcggc tgccacagcg cttgtgaccg cggtcagcct ggccgccccc gctcatgccg    3612 ccaacccta cgagcgcggc cccaacccga ccgacgcct gctcgaagcc cgcagcggcc     3672
ccttctccgt gagtgaagaa cgggcctccc gcttcggtgc tgacggtttc ggcggcggca    3732
ccatctacta cccgcgggag aacaacacct acggtgccgt ggcgatctcc cccggctaca    3792
ccggcaccca ggcctctgtc gcctggctgg gcaagcgcat cgcctcccac ggcttcgtcg    3852
tcatcaccat cgacaccaac accaccctcg accagccgga cagccgggcc cgccagctca    3912
acgccgcgct ggactacatg atcaacgacg cctcgtccgc ggtgcgcagc cggatcgaca    3972
gcagccgact ggcggtcatg ggccactcca tgggcggcgg cggcagcctg cgtctggcct    4032
cccagcgtcc cgacctgaag gccgccatcc cgctcacccc gtggcacctc aacaagaact    4092
ggagcagtgt gcgggttccc accctcatca tcggtgctga cctggacacc atcgctccgg    4152
tcctcaccca cgcccggccc ttctacaaca gcctcccgac ctcgatcagc aaggcctacc    4212
tggagctgga cggcgcaacc cacttcgccc cgaacatccc caacaagatc atcggcaagt    4272
acagcgtcgc ctggctcaag cggttcgtcg acaacgacac ccgctacacc cagttcctct    4332
gccccggacc gcgcgacgga ctcttcggcg aggtcgaaga gtaccgctcc acctgccccct   4392 tctaggcggt agggtcccgc agcgagtcag caagatctcc ttcccggtgg ttgatactg     4451
```

<210> SEQ ID NO 5
<211> LENGTH: 301
<212> TYPE: PRT
<213> ORGANISM: Thermobifida fusca

<400> SEQUENCE: 5

Met Ala Val Met Thr Pro Arg Arg Glu Arg Ser Ser Leu Leu Ser Arg
1               5                   10                  15

Ala Leu Gln Val Thr Ala Ala Ala Thr Ala Leu Val Thr Ala Val
            20                  25                  30

Ser Leu Ala Ala Pro Ala His Ala Ala Asn Pro Tyr Glu Arg Gly Pro
        35                  40                  45

Asn Pro Thr Asp Ala Leu Leu Glu Ala Ser Ser Gly Pro Phe Ser Val
    50                  55                  60

Ser Glu Glu Asn Val Ser Arg Leu Ser Ala Ser Gly Phe Gly Gly Gly
65                  70                  75                  80

```
Thr Ile Tyr Tyr Pro Arg Glu Asn Asn Thr Tyr Gly Ala Val Ala Ile
                85                  90                  95

Ser Pro Gly Tyr Thr Gly Thr Glu Ala Ser Ile Ala Trp Leu Gly Glu
            100                 105                 110

Arg Ile Ala Ser His Gly Phe Val Ile Thr Ile Asp Thr Ile Thr
            115                 120                 125

Thr Leu Asp Gln Pro Asp Ser Arg Ala Glu Gln Leu Asn Ala Ala Leu
    130                 135                 140

Asn His Met Ile Asn Arg Ala Ser Ser Thr Val Arg Ser Arg Ile Asp
145                 150                 155                 160

Ser Ser Arg Leu Ala Val Met Gly His Ser Met Gly Gly Gly Gly Thr
                165                 170                 175

Leu Arg Leu Ala Ser Gln Arg Pro Asp Leu Lys Ala Ala Ile Pro Leu
            180                 185                 190

Thr Pro Trp His Leu Asn Lys Asn Trp Ser Ser Val Thr Val Pro Thr
            195                 200                 205

Leu Ile Ile Gly Ala Asp Leu Asp Thr Ile Ala Pro Val Ala Thr His
    210                 215                 220

Ala Lys Pro Phe Tyr Asn Ser Leu Pro Ser Ser Ile Ser Lys Ala Tyr
225                 230                 235                 240

Leu Glu Leu Asp Gly Ala Thr His Phe Ala Pro Asn Ile Pro Asn Lys
            245                 250                 255

Ile Ile Gly Lys Tyr Ser Val Ala Trp Leu Lys Arg Phe Val Asp Asn
            260                 265                 270

Asp Thr Arg Tyr Thr Gln Phe Leu Cys Pro Gly Pro Arg Asp Gly Leu
            275                 280                 285

Phe Gly Glu Val Glu Glu Tyr Arg Ser Thr Cys Pro Phe
    290                 295                 300

<210> SEQ ID NO 6
<211> LENGTH: 31
<212> TYPE: DNA
<213> ORGANISM: artificial sequence
<220> FEATURE:
<223> OTHER INFORMATION: Amorce sens_site de restriction BamHI

<400> SEQUENCE: 6
gatcggatcc gccacgtcca gcgcttgtcc g                              31

<210> SEQ ID NO 7
<211> LENGTH: 34
<212> TYPE: DNA
<213> ORGANISM: artificial sequence
<220> FEATURE:
<223> OTHER INFORMATION: Amorce anti-sens_site de restriction XhoI

<400> SEQUENCE: 7
ccggaactcg agggccgacc cgccaagctt gttg                           34
```